(12) United States Patent
Kim et al.

(10) Patent No.: US 10,556,819 B2
(45) Date of Patent: Feb. 11, 2020

(54) METHOD FOR PREPARING GLASS-CERAMICS, CAPABLE OF ADJUSTING MACHINABILITY OR TRANSLUCENCY THROUGH CHANGE IN TEMPERATURE OF HEAT TREATMENT

(71) Applicant: HASS CO., LTD, Gangneung-si, Gangwon-do (KR)

(72) Inventors: Yong Su Kim, Gangneung-si (KR); Hyun Jun Jeon, Busan (KR); Hyung Bong Lim, Ansan-si (KR); Kyung Sik Oh, Incheon (KR); Sung Min Kim, Yongin-si (KR); Young Pyo Hong, Gangneung-si (KR); Joon Hyung Kim, Anseong-si (KR)

(73) Assignee: HASS CO., LTD, Gangneung-si (KR)

( * ) Notice: Subject to any disclaimer, the term of this patent is extended or adjusted under 35 U.S.C. 154(b) by 121 days.

(21) Appl. No.: 15/453,296

(22) Filed: Mar. 8, 2017

(65) Prior Publication Data
US 2018/0257973 A1  Sep. 13, 2018

(51) Int. Cl.
| | | |
|---|---|---|
| C03B 32/02 | (2006.01) | |
| C03C 3/097 | (2006.01) | |
| C03C 4/02 | (2006.01) | |
| C03C 4/00 | (2006.01) | |
| C03C 10/00 | (2006.01) | |

(52) U.S. Cl.
CPC ............. *C03B 32/02* (2013.01); *C03C 3/097* (2013.01); *C03C 4/0021* (2013.01); *C03C 4/02* (2013.01); *C03C 10/0027* (2013.01)

(58) Field of Classification Search
None
See application file for complete search history.

(56) References Cited

U.S. PATENT DOCUMENTS

| | | |
|---|---|---|
| 3,804,608 A | 4/1974 | Gaskell et al. |
| 4,189,325 A | 2/1980 | Barrett et al. |
| 4,515,634 A | 5/1985 | Wu et al. |
| 5,219,799 A | 6/1993 | Beall et al. |
| 5,744,208 A | 4/1998 | Beall et al. |
| 5,804,520 A | 9/1998 | Morinaga et al. |
| 5,968,856 A | 10/1999 | Schweiger et al. |
| 6,200,137 B1 * | 3/2001 | Holand ................ C03C 4/0021 427/2.29 |
| 6,342,458 B1 | 1/2002 | Schweiger et al. |
| 6,372,319 B1 | 4/2002 | Abe et al. |
| 6,375,729 B1 | 4/2002 | Brodkin et al. |
| 6,420,288 B2 | 7/2002 | Schweiger et al. |
| 6,455,451 B1 | 9/2002 | Brodkin et al. |
| 6,495,480 B1 | 12/2002 | Goto |
| 6,514,893 B1 | 2/2003 | Schweiger et al. |
| 6,517,623 B1 | 2/2003 | Brodkin et al. |
| 6,606,884 B2 | 8/2003 | Schweiger et al. |
| 6,802,894 B2 | 10/2004 | Brodkin et al. |
| 6,818,573 B2 | 11/2004 | Petticrew |
| 2015/0374465 A1 | 12/2015 | Bürke et al. |
| 2015/0374589 A1 | 12/2015 | Rampf et al. |

FOREIGN PATENT DOCUMENTS

| | | |
|---|---|---|
| EP | 1253116 A1 | 10/2002 |
| EP | 1005841 B1 | 2/2005 |
| EP | 1534169 B1 | 3/2006 |
| EP | 3135269 A1 | 3/2017 |
| JP | 2000-086289 A | 3/2000 |
| JP | 2011-225441 A | 11/2011 |
| JP | 2012-250911 A | 12/2012 |
| KR | 10-2012-0073710 A | 7/2012 |
| KR | 10-1262121 B1 | 5/2013 |

* cited by examiner

*Primary Examiner* — Cynthia Szewczyk
(74) *Attorney, Agent, or Firm* — Novick, Kim & Lee, PLLC; Sang Ho Lee

(57) ABSTRACT

The present invention relates to a method for preparing a lithium disilicate glass-ceramics containing silicate as a main component, and more particularly, to a method for preparing a glass-ceramics, which is capable of adjusting machinability or translucency according to a crystalline size by using a first heat treatment or a second heat treatment. To this end, a method for preparing a glass-ceramics containing a silica crystalline phase includes: performing a first heat treatment on a glass composition at a temperature of 400 to 850° C., so that a lithium disilicate crystalline phase and a silica crystalline phase each having a size of 5 to 2,000 nm are formed through the first heat treatment. After the first heat treatment, the method further includes performing a second heat treatment at a temperature of 780 to 880° C., so that translucency is adjusted by a temperature of the second heat treatment.

2 Claims, 3 Drawing Sheets

METHOD FOR PREPARING GLASS-CERAMICS, CAPABLE OF ADJUSTING MACHINABILITY OR TRANSLUCENCY THROUGH CHANGE IN TEMPERATURE OF HEAT TREATMENT

BACKGROUND OF THE INVENTION

Field of the Invention

The present invention relates to a method for preparing a lithium disilicate glass-ceramics containing silicate as a main component, and more particularly, to a method for preparing a glass-ceramics, which is capable of adjusting a crystalline size, translucency, and machinability by using a first heat treatment or a second heat treatment.

Description of the Related Art

With economic development and increased income, an interest in appearance has been increased, and an interest in aesthetics of dental prosthetic materials has been increased in response to the interest in appearance. As a result, various kinds of dental prosthetic restoration materials with the aesthetics are introduced, and among them, various non-metal crown materials without using metals have been developed.

The crown materials mean prosthetic materials for restoring enamel and dentin parts of the damaged tooth. The crown materials are classified into inlay, onlay, veneer, crown, and the like according to an applied region. Since the region restored by the crown material is the outer surface of the tooth, the aesthetics is highly required and the high strength is required due to fractures such as abrasion and chipping of antagonist teeth. Materials which are used as the crown materials in the related art are leucite glass-ceramics, reinforced porcelain, or fluorapatite ($Ca_5(PO_4)_3F$) glass-ceramics. Even thought the materials have the excellent aesthetics, there is a disadvantage in that the possibility of fracture is high due to low strength of 80 to 120 MPa. Therefore, currently, studies of developing various high-strength crown materials have been conducted.

Lithium silicate glass-ceramics was introduced by Marcus P. Borom and Anna M. Turkalo (The Pacific Coast Regional Meeting, The American Ceramic Society, San Francisco, Calif., Oct. 31, 1973 (Glass division, No. 3-G-73P)) in 1973. The formation of various crystalline nuclei and the crystalline and the strength for each growth heat treatment condition were studies by using $Li_2O$—$Al_2O_3$—$SiO_2$—$Li_2O$—$K_2O$—$B_2O_3$—$P_2O_5$-based glasses. When the high-temperature lithium disilicate crystalline is shown from low-temperature lithium metasilicate, the strength of 30 to 35 Kpsc (kilogram per square centimeter: $Kg/cm^2$) is shown. The strength is caused by residual stress due to a difference in thermal expansion coefficient between base glass, mother glass, $Li_2SiO_5$, and $Li_2SiO_3$ crystals.

A material and a method for manufacturing an artificial tooth (monolithic dental crown) by using glass containing a lithium disilicate crystal are disclosed in a plurality of patent documents. However, according to the known techniques, due to a coarse crystalline phase, it is difficult to directly machine the glass containing the lithium disilicate crystal. In order for machining, it is necessary to primarily form and machine a lithium metasilicate crystalline phase (machinable crystalline) and secondarily form a high-strength lithium disilicate crystalline phase by performing a heat treatment. Thus, dimension accuracy is lowered due to shrinkage caused by the heat treatment, and it is inconvenient to additionally perform the heat treatment. Generally, since CAD/CAM machining is directly performed in a dental clinic and needs to be applied to a patient as quickly as possible (one-day appointment), a time delay due to a heat treatment imposes financial difficulties on a patient and a user.

In addition, since an existing lithium disilicate glass-ceramic material has a coarse crystalline phase, there is a limitation in realizing high light transmittance or opalescence similar to those of a natural tooth.

In particular, in order to machine the existing lithium disilicate glass-ceramic material, lithium metasilicate glass-ceramics having excellent machinability are primarily prepared, and then, lithium disilicate is prepared through a secondary crystallization heat treatment to improve strength. In this case, a crystalline phase has a size of 3 μm or more. In this state, machinability is considerably lowered and only high strength is obtained.

SUMMARY OF THE INVENTION

An aspect of the present invention is directed to propose a method for preparing a glass-ceramics containing a lithium disilicate crystalline phase, a silicate crystalline phase, and a silica crystalline phase, which have excellent machinability, by adjusting a (nanoscale) crystalline size through a change in a temperature of a first heat treatment.

Another aspect of the present invention is directed to propose a method for preparing a glass-ceramics, which is capable of adjusting translucency by adjusting crystalline sizes of lithium disilicate, silicate, and silica, which have a nano crystalline phase.

According to an embodiment of the present invention, a glass composition includes: 60 to 83 wt % $SiO_2$; 10 to 15 wt % $Li_2O$; 2 to 6 wt % $P_2O_5$ working as a nuclei formation agent; 1 to 5 wt % $Al_2O_3$ for increasing a glass transition temperature and a softening point and enhancing chemical durability of a glass; 0.1 to 3 wt % SrO for increasing the softening point of the glass; 0.1 to 2 wt % ZnO; 1 to 5 wt % colorants; and 2.5 to 6 wt % alkali and alkaline-earth mixture ($Na_2O+K_2O$) for increasing a thermal expansion coefficient of the glass.

According to an embodiment of the present invention, a method for preparing a glass-ceramics containing a silica crystalline phase includes performing a first heat treatment on a glass composition at a temperature of 400 to 850° C., so that a lithium disilicate crystalline phase and a silica crystalline phase each having a size of 5 to 2,000 nm are formed through the first heat treatment.

According to an embodiment of the present invention, the method further includes, after the first heat treatment, performing a second heat treatment at a temperature of 780 to 880° C., so that translucency is adjusted by a temperature of the second heat treatment.

DETAILED DESCRIPTION OF EMBODIMENTS

Figure 1:
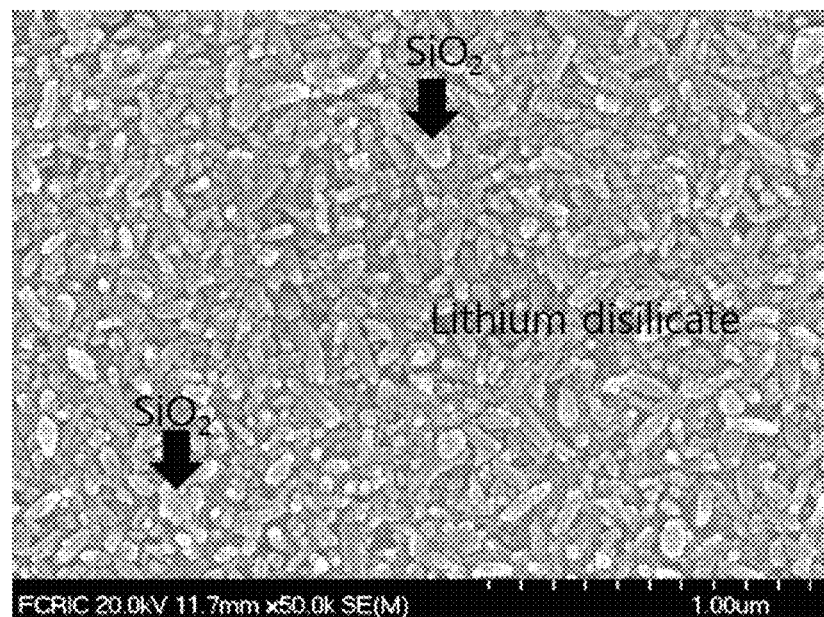
FIG. 1 is a scanning electron microscope (SEM) image of a microstructure when a first heat treatment was performed on a starting raw material.

The present invention relates to a glass material, whose crystalline size is adjustable through a temperature of a heat treatment, and a method for preparing a glass-ceramics for a dental material. The dental material is applicable only when it has translucent aesthetics and machinability. The present invention is directed to obtain aesthetics and machinability required by the dental material by developing a glass composition, whose crystalline size and crystal distribution are adjustable according to a temperature of a heat treatment.

A high-strength glass-ceramics for a tooth according to the present invention includes a silica crystalline phase, a lithium disilicate crystal, and hyaline. Since the high-strength glass-ceramics exhibits a very similar color to that of a natural tooth as a whole, the high-strength glass-ceramics is highly aesthetic and is suitable for use as a dental material.

The aesthetics, particularly, light transmittance is largely affected by the degree of light scattering caused by a difference in refractive index between different crystallines in dense bulk. The $SiO_2$ cluster has a refractive index of 1.48. As a content of the $SiO_2$ cluster increases, an interface between the $SiO_2$ cluster and mother glass or a lithium disilicate crystalline phase increases. Accordingly, transmittance decreases due to high scattering of light. Therefore, in order to obtain light-transmitting properties usable for the dental material, a prosthetic material having various light-transmitting properties may be prepared by forming an appropriate amount of only a $SiO_2$ cluster crystalline phase within a glass.

In the case of an existing lithium disilicate glass-ceramics, a prosthesis has been manufactured by primarily forming a lithium metasilicate glass-ceramics having low strength of 220 MPa or less, machining the lithium metasilicate glass-ceramics, and increasing strength to 350 MP through a secondary heat treatment. However, since these translucencies have already been determined according to a composition or the like in a block state, as many products and quantities as the number of required translucencies are required, and the number of implementable translucencies is limited.

The present invention proposes a material that is machinable in a state of lithium disilicate rather than an existing lithium metasilicate crystalline phase by forming a lithium disilicate crystalline phase and a silica crystalline phase having a nanosize. At the same time, machinability and transmittance may be adjusted according to a crystallization temperature. Therefore, it is possible to manufacture a product having desired transmittances at different temperatures in one product and also manufacture a product having various translucencies in one product. Due to a crystal grown after a second heat treatment, mechanical properties are increased, and in particular, biaxial flexure strength of 490 MPa or more is exhibited.

This may meet needs of customers who want various translucencies, and physical properties also are improved compared to an existing product.

According to the present invention, a glass containing a silica crystalline phase includes 60 to 83 wt % $SiO_2$, 10 to 15 wt % $Li_2O$, 2 to 6 wt % $P_2O_5$ working as a nuclei formation agent, 1 to 5 wt % $Al_2O_3$ for increasing a glass transition temperature and a softening point and enhancing chemical durability of the glass, 0.1 to 3 wt % SrO for increasing the softening point of the glass, 0.1 to 2 wt % ZnO, 1 to 5 wt % colorants, and 2.5 to 6 wt % alkali and alkaline-earth mixture ($Na_2O+K_2O$) for increasing a thermal expansion coefficient of the glass.

The dental high-strength glass-ceramics according to the exemplary embodiment of the present invention may further include 1 to 5 wt % colorant as described above in order to provide the same or similar color as or to the teeth. The colorant is to provide the same or similar color and fluorescence as or to the teeth and may use red iron oxide ($Fe_2O_3$), yellow ceria ($CeO_2$), orange vanadium pentoxide ($V_2O_5$), black vanadium trioxide $V_2O_3$, $Er_2O_3$, $Tb_2O_3$, $Pr_2O_3$, $TaO_2$, $MnO_2$, or a mixture thereof. For example, red iron oxide ($Fe_2O_3$), ceria ($CeO_2$), or vanadium pentoxide ($V_2O_5$) is added together with starting materials to be melted to have a light yellow which is similar to the teeth's color. Titanium oxide ($TiO_2$) has white to provide a very similar color to the teeth's color.

The aforementioned starting materials are measured and mixed. In this case, $Li_2CO_3$ instead of $Li_2O$ may be added and carbon dioxide ($CO_2$) as a carbon (C) component of $Li_2CO_3$ is discharged and removed as gas in a melting process of the glass. Further, in alkali oxide, $K_2CO_3$ and $Na_2CO_3$ instead of $K_2O$ and $Na_2O$ may be added, respectively, and carbon dioxide ($CO_2$) as carbon (C) components of $K_2CO_3$ and $Na_2CO_3$ is discharged and removed as gas in a melting process of the glass.

The mixing process uses a dry mixing process, and a ball milling process and the like may be used as the dry mixing process. When describing the ball milling process in detail, the starting materials are put in a ball milling machine and mechanically grinded and uniformly mixed by rotating the ball milling machine at a predetermined speed. The balls used in the ball milling machine may use balls made of ceramic materials such as zirconia or alumina, and the sizes of the balls may be the same as each other or has at least two sizes. The size of the ball, milling time, rpm of the ball milling machine, and the like are controlled by considering a desired size of the particle. In an example, taking into account a particle size, a size of a ball may be set to a range of 1 to 30 mm, and a rotational speed of a ball milling machine may be set to a range of 50 to 500 rpm. Taking into account a targeted particle size or the like, it is desirable that ball milling is performed for 1 to 48 hours. A starting raw material is pulverized into fine particles through the ball milling, and the fine particles have a uniform particle size and are also uniformly mixed.

The mixed starting material is put in a melting furnace and melted by heating the melting furnace with the starting material. Herein, the melting means that the starting materials are changed into a material state having viscosity in a liquid state other than a solid state. It is preferred that the melting furnace is made of a material having a high melting point, a large strength, and a low contact angle in order to suppress a molten material from being attached. To this end, it is preferred that the melting furnace is a melting furnace made of a material such as platinum (Pt), diamond-like-carbon (DLC), and chamotte or coated on the surface with a material such as platinum (Pt) or diamond-like-carbon (DLC).

The melting is performed for 1 to 12 hours at atmospheric pressure. When the melting temperature is less than 1,400° C., the starting materials may not be melted. When the melting temperature is more than 2,000° C., the starting materials are not economic due to excessive energy consumption, and thus, it is preferred that the starting materials are melted in the aforementioned range. Further, when the melting time is too short, the starting materials may not be sufficiently melted, and when the melting time is very large, the starting materials are not economic due to excessive energy consumption. It is preferred that the heating rate of the melting furnace is 5 to 50° C./min. When the heating rate of the melting furnace is very slow, a lot of time is taken and thus, productivity is deteriorated, and when the heating rate of the melting furnace is very fast, the volatile amount of the starting materials is increased, and thus, the property of the glass-ceramics may be bad. As a result, it is preferred that the temperature of the melting furnace is increased at the heating rate in the aforementioned range. It is preferred that the melting is performed at an oxygen atmosphere such as air.

In order to obtain the dental glass-ceramics having desired shape and size, the molten material is poured in a predetermined mold. It is preferred that the mold is made of a material having a high melting point, a large strength, and a low contact angle for suppressing the glass molten material from being attached. To this end, the mold is made of a material such as graphite and carbon, and it is preferred that the molten material is preheated at 200 to 300° C. and poured in the mold in order to prevent thermal shock.

When a molten material contained in a mold is cooled to a temperature of 60 to 100° C., the cooled molten material is transferred to a crystallization heat treatment furnace and a glass-ceramics is prepared by performing nuclei formation and crystal growth on the glass. This is because, in a method capable of variously adjusting machinability and translucency of the glass through first and second heat treatments as proposed in the present invention, a crystalline size in the glass-ceramics is adjustable according to a temperature. A crystalline phase formed after the first heat treatment includes a lithium disilicate crystalline phase and a silica crystalline phase each having a crystalline size of 5 to 2,000 nm at a temperature of 400 to 850° C. Machinability of cutting force may be obtained when a crystalline phase (lithium disilicate or silica) has a crystalline size of 30 to 500 nm corresponding to a temperature of 480 to 800° C.

When a final prosthesis is completed through the second heat treatment, a clinical treatment needs products having various translucencies. At this time, transmittance generally corresponds to 20 to 55% (at a wavelength of 550 nm). When the second heat treatment was performed at a temperature of 780 to 900° C., transmittance was 55 to 18% (at a wavelength of 550 nm). Transmittance was reduced at a temperature of 880° C. or more, and it was analyzed that transmittance applicable to a clinical treatment was obtained at a temperature of 780 to 880° C. At this time, a size of a crystalline phase (lithium disilicate crystalline phase or silica crystalline phase) corresponds to 0.3 to 5.5 μm and transmittance was 27 to 55% (at a wavelength of 550 nm).

Therefore, the present invention proposes a method for preparing glass, capable of adjusting machinability and translucency, which are actually usable for a clinical treatment, through the first and second heat treatments, and a heat treatment condition.

FIG. 1 is a scanning electron microscope (SEM) image of a microstructure when a first heat treatment was performed on a starting raw material, and in particular, the first heat treatment was performed at a temperature 750° C. Referring to FIG. 1, it can be seen that, when the first heat treatment was performed at a temperature of 750° C., there existed a globular $SiO_2$ crystalline phase having a similar size to acicular lithium disilicate having a size of about 100 to about 2,000 nm. That is, it can be seen that, when the first heat treatment was performed on a general starting raw material, there existed no globular $SiO_2$ crystalline phase, but when the first heat treatment was performed on the starting raw material proposed in the present invention, there existed the globular $SiO_2$ crystalline phase.

Figure 2:
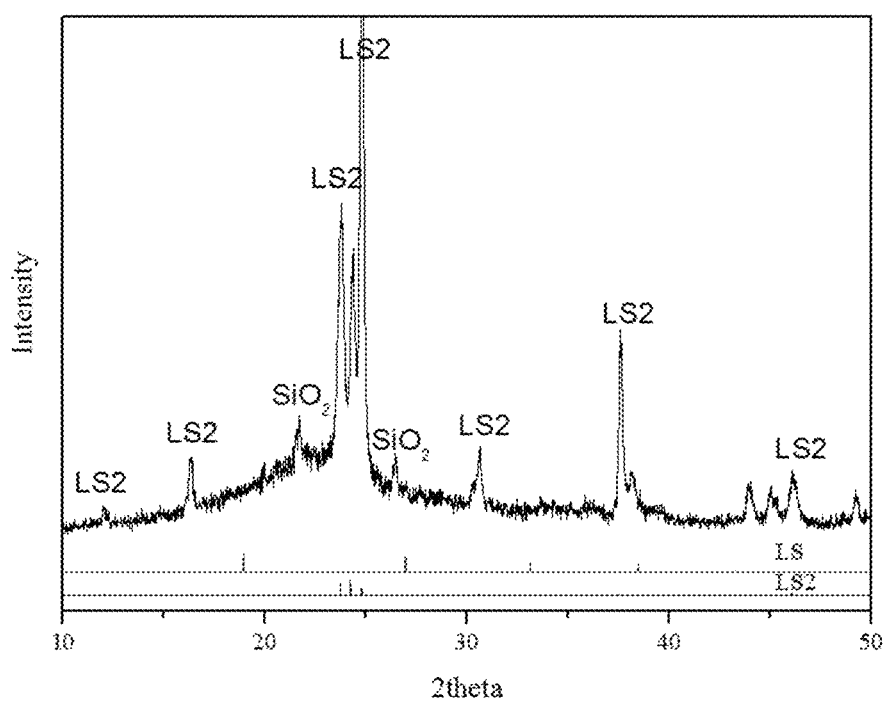
FIG. 2 is a graph showing an X-ray diffraction analysis of a crystalline phase when a first heat treatment was performed on a starting raw material.

FIG. 2 is a graph showing an X-ray diffraction analysis of a crystalline phase when a first heat treatment was performed on a starting raw material, and in particular, the first heat treatment was performed at a temperature of 750° C. Referring to FIG. 2, it can be seen from the X-ray diffraction analysis that crystals shown in FIG. 1 were a lithium disilicate crystal and a $SiO_2$ crystal.

Figure 3:
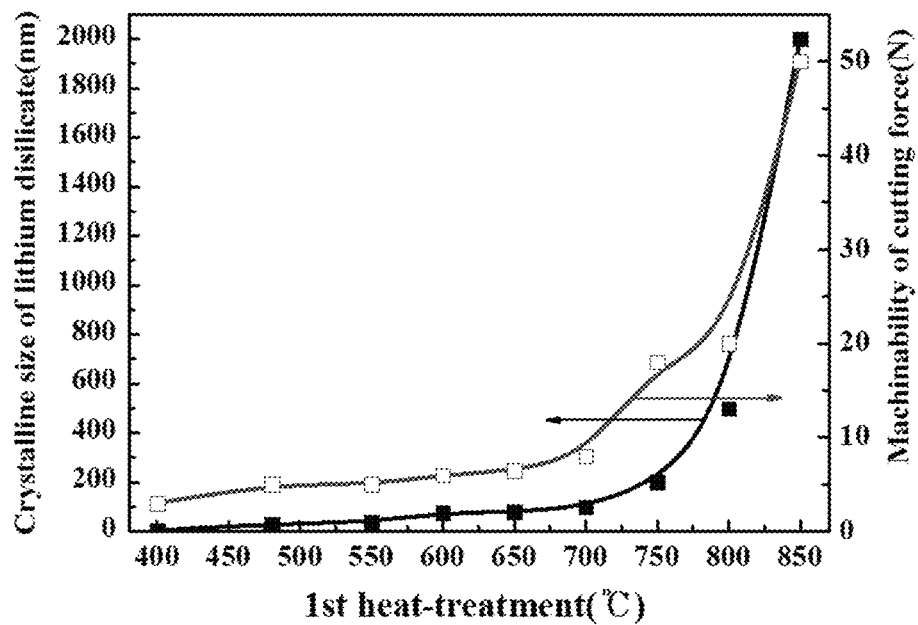
FIG. 3 is a graph showing measurement results of a crystalline size and machining resistance (machinability of cutting force) of lithium disilicate according to a temperature of a first heat treatment.

FIG. 3 is a graph showing measurement results of a crystalline size and machining resistance (machinability of cutting force) of lithium disilicate according to a temperature of a first heat treatment. Referring to FIG. 3, a black graph indicates a crystalline size of lithium disilicate, and a red graph indicates a cutting force. According to the graphs, it can be confirmed that, as a crystalline size increases, a cutting force increases. When the cutting force increases, a high load is applied to a cutting bur, thus deteriorating machinability. Therefore, according to the present invention, it can be seen that a crystalline phase having a size of 30 to 500 nm corresponding to a temperature of 480 to 800° C. has excellent machinability.

Figure 4:
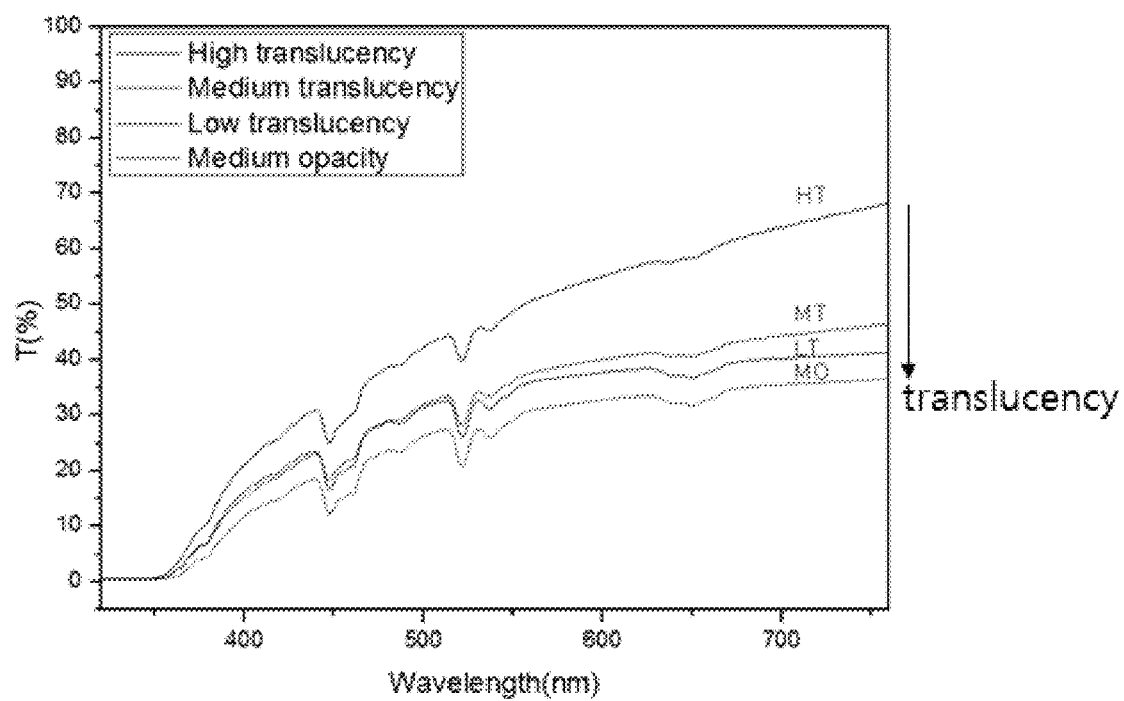
FIG. 4 is a graph showing translucency spectrum result data according to a temperature of a second heat treatment.

FIG. 4 is a graph showing translucency spectrum result data according to a temperature of a second heat treatment.

A lithium disilicate crystalline phase and the silica crystalline phase each have high translucency at a temperature of 780 to 820° C., medium translucency at a temperature of 821 to 840° C., low translucency at a temperature of 841 to 860° C., and medium opacity at a temperature of 861 to 880° C., and a retention time is 1 minute to 2 hours. Referring to FIG. 4, as a temperature increases, translucency decreases from high translucency to medium opacity.

Figure 5:
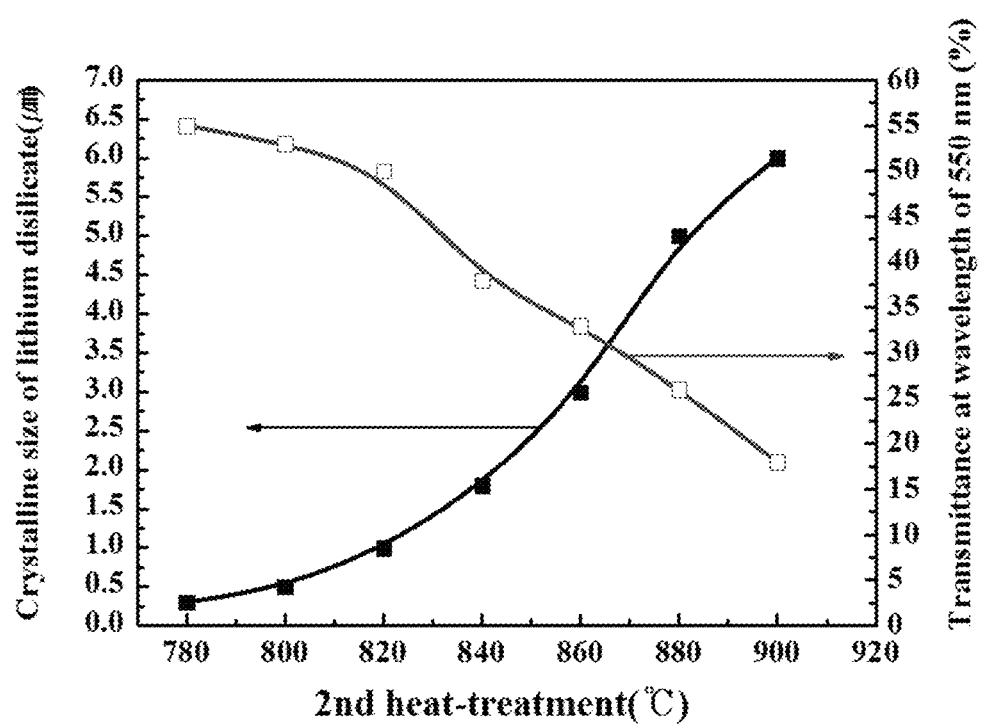
FIG. 5 is a graph showing measurement results of a crystalline size and transmittance of lithium disilicate according to a temperature of a second heat treatment.

FIG. 5 is a graph showing measurement results of a crystalline size and transmittance of lithium disilicate according to a temperature of a second heat treatment. The present invention is characterized in that transmittance is adjustable according to a temperature of a heat treatment with respect to a glass-ceramics. In the case of FIG. 5, a black graph indicates a crystalline size of lithium disilicate, and a red graph indicates transmittance. It can be seen from FIG. 5 that as the temperature of the second heat treatment increases, the crystalline size increases, and as the crystalline size increases, transmittance decreases. As the crystalline size increases, a ratio of absorption and reflection of light further increase rather than transmission of light, thus reducing the transmittance. Therefore, it can be confirmed that it is possible to prepare a glass-ceramics exhibiting various transmittances according to a change in the temperature of the second heat treatment even in the glass-ceramics having one composition.

Machinability and translucency of glass proposed in the present invention may be variously adjusted through a first heat treatment or a second heat treatment. Generally, a crystalline size in a glass-ceramics may be adjusted according to a temperature. According to the present invention, a lithium disilicate crystalline phase and a silica crystalline phase are formed through a first heat treatment. In particular, a crystalline phase formed through the first heat treatment is formed at a temperature of 480 to 800° C. so as to increase machinability of cutting force. At this time, the formed crystalline phase has a size of 30 to 500 nm.

In addition, when a final prosthesis is completed, a clinical treatment needs products having various translucencies. The present invention proposes a product having transmittance of 27 to 55% (at a wavelength of 550 nm) through the second heat treatment.

As described above, the present invention proposes a method for preparing a glass-ceramics, capable of adjusting machinability and translucency, which are actually usable for a clinical treatment, through the first and second heat treatment conditions.

While the present invention has been described with reference to an embodiment, it will be apparent to those skilled in the art that various changes and modifications may be made without departing from the spirit and scope of the inventive concept.

What is claimed is:

1. A method for preparing a glass-ceramics containing a silica crystalline phase, the method comprising:
   performing a first heat treatment on a glass composition at a temperature of 480 to 800° C., so that a lithium disilicate crystalline phase and a silica crystalline phase each having a size of 30 to 500 nm are formed through the first heat treatment; and
   performing a second heat treatment at a temperature of 780 to 880° C., so that translucency of the glass ceramics is adjusted based on the temperature of the second heat treatment,
   wherein the glass composition comprises:
   60 to 83 wt % $SiO_2$;
   10 to 15 wt % $Li_2O$;
   2 to 6 wt % $P_2O_5$ working as a nuclei formation agent;
   1 to 5 wt % $Al_2O_3$ for increasing a glass transition temperature and a softening point and enhancing chemical durability of glass;
   0.1 to 3 wt % SrO for increasing the softening point of the glass;
   0.1 to 2 wt % ZnO;
   1 to 5 wt % colorants; and
   2.5 to 6 wt % mixture of $Na_2O$ and $K_2O$ for increasing a thermal expansion coefficient of the glass,
   wherein the lithium disilicate crystalline phase and the silica crystalline phase each have a transmittance of 18 to 55% at a wavelength of 550 nm, and have a first translucency value at a temperature of 780 to 820° C., a second translucency value at a temperature of 821 to 840° C., a third translucency value at a temperature of 841 to 860° C., and a fourth translucency value at a temperature of 861 to 880° C. depending on the temperature of the second heat treatment,
   wherein the translucency values satisfy the following expression 1:

$$HT > MT > LT > MO$$

where HT is the first translucency value, MT is the second translucency value, LT is the third translucency value, and MO is the fourth translucency value, and
   wherein a retention time is 1 minute to 2 hours.

2. The method of claim 1, wherein the lithium disilicate crystalline phase and the silica crystalline phase each have a size of 0.3 to 5.5 μm after the second heat treatment.

* * * * *